US00PP12217P2

(12) United States Plant Patent
Geers

(10) Patent No.: US PP12,217 P2
(45) Date of Patent: Nov. 20, 2001

(54) WEIGELA PLANT NAMED 'ELVERA'

(75) Inventor: Herman Geers, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 09/422,172

(22) Filed: Oct. 22, 1999

(51) Int. Cl.[7] ..... A01H 5/00

(52) U.S. Cl. ..... Plt./226
(58) Field of Search ..... Plt./226

*Primary Examiner*—Bruce R. Campell
*Assistant Examiner*—A Para
(74) *Attorney, Agent, or Firm*—C. A. Whealy

(57) ABSTRACT

A distinct cultivar of Weigela plant named 'Elvera', characterized by its dwarf, low mounded plant habit; freely branching; dense and bushy growth habit; very dark leaves that appear metallic during the late summer; and resistant to pathogens common to *Weigela florida*.

1 Drawing Sheet

BACKGROUND OF THE INVENTION

The present invention relates to a new and distinct cultivar of Weigela plant, botanically known as *Weigela florida*, and hereinafter referred to by the cultivar name Elvera.

The new cultivar is a product of a planned breeding program conducted by the Inventor in Boskoop, The Netherlands. The objective of the breeding program is to create new Weigela cultivars having dwarf plant habit and dark-colored leaves.

The new cultivar originated from a cross made by the Inventor in 1993, in Boskoop, The Netherlands, of the nonpatented cultivar Victoria as the female, or seed, parent with an unnamed proprietary Weigela selection, as the male, or pollen, parent.

The cultivar Elvera was discovered and selected by the Inventor as a single plant within the progeny of the stated cross in a controlled environment in Boskoop, The Netherlands. The selection of this plant was based on its dwarf growth habit and dark-colored leaves.

Asexual reproduction of the new cultivar by terminal cuttings taken at Boskoop, The Netherlands, has shown that the unique features of this new Weigela are stable and reproduced true to type in successive generations.

SUMMARY OF THE INVENTION

Plants of the cultivar Elvera have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Elvera'. These characteristics in combination distinguish 'Elvera' as a new and distinct cultivar:

1. Dwarf, low mounded plant habit.

2. Freely branching; dense and bushy growth habit.

3. Very dark leaves that appear metallic during the late summer.

4. Relatively resistant to pathogens common to *Weigela florida*.

Compared to plants of the female parent, the cultivar Victoria, plants of the new Weigela are much more dwarf, broader and more freely branching. In addition, plants of the new Weigela have significantly darker-colored leaves and darker pink and smaller flowers than plants of the cultivar Victoria.

Compared to plants of the male parent, the unnamed proprietary *Weigela florida* selection, plants of the new Weigela are more dwarf and more freely branching. In addition, plants of the new Weigela have darker-colored leaves than plants of the unnamed proprietary selection.

Plants of the new Weigela can be compared to plants of the commercial cultivar *Weigela florida* Alexandra, disclosed in U.S. Plant Pat. No. 10,772. However, in side-by-side comparisons conducted in Grand Haven, Mich., plants of the new Weigela differed from plants of the cultivar Alexandra in the following characteristics:

1. Plants of the new Weigela are more dwarf and more mounded, less upright, than plants of the cultivar Alexandra.

2. Plants of the new Weigela are more slower growing than plants of the cultivar Alexandra and require less pruning.

3. Plants of the new Weigela are have finer branches and leaves than plants of the cultivar Alexandra.

4. Leaves of plants of the new Weigela have a metallic sheen whereas leaves of plants of the cultivar Alexandra do not have a metallic sheen.

Plants of the new Weigela can be compared to plants of the nonpatented *Weigela florida* 'Purpurea nana'. However, in side-by-side comparisons conducted in Grand Haven, Mich., plants of the new Weigela differed from plants of the cultivar Purpurea nana in the following characteristics:

1. Plants of the new Weigela have a more dwarf and less upright growth habit than plants of the cultivar Purpurea nana.

2. Plants of the new Weigela are have a richer pink flower color than plants of the cultivar Purpurea nana.

3. Leaf color of plants of the new Weigela is darker than leaf color of plants of the cultivar Purpurea nana.

4. Leaf color of plants of the new Weigela becomes darker during the summer whereas leaf color of plants of the cultivar Purpurea nana fades during the summer.

5. Leaves of plants of the new Weigela are glossy and have a metallic sheen whereas leaves of plants of the cultivar Purpurea nana are not glossy and do not have a metallic sheen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of typical plants of the new Weigela.

The photograph at the bottom of the sheet comprises a close-up view of typical leaves of the new Weigela. Foliage colors in the photographs appear lighter than the actual colors due to light reflectance.

DETAILED BOTANICAL DESCRIPTION

In the following description, color reference are made to The Royal Horticultural Society Colour Chart except where general terms of ordinary dictionary significance are used. One-year old plants were used for the description and were grown in one-gallon containers under production conditions which closely approximate commercial production conditions in Grand Haven, Mich. Plants were grown in an outdoor nursery without shading.

Botanical classification: *Weigela florida* cultivar Elvera.

Parentage:

*Female parents.*—*Weigela florida* cultivar Victoria, not patented.

*Male parent.*—Unnamed proprietary *Weigela florida* selection.

Propagation:

*Type cutting.*—Terminal vegetative cuttings.

*Time to initiate roots.*—About 20 days during the summer at 17 to 20° C.

*Time to produce a rooted liner.*—About 90 days during the summer at 17 to 20° C.

*Root description.*—Fine.

Plant description:

*Crop time.*—From rooted liners, about one year is required to produce a fully-grown flowering plant in an one-gallon container.

*Form.*—Low mounded, compact; dense and bushy. Appropriate for one to three-gallon containers.

*Branching habit.*—Very freely branching, pinching is usually not required.

*Plant height* (*from soil level to top of plant plane*).—About 20 to 40 cm.

*Area of spread.*—About 40 to 80 cm.

*Vigor.*—Moderate.

*Lateral branches.*—Internode length: About 1.5 cm. Texture: Pubescent. Color: Gray, 201A.

*Foilage description.*—Leaves simple, generally symmetrical, opposite and long persisting. Length: About 5.5 cm. Width: About 3 cm. Shape: Elliptic. Apex: Acute to apiculate. Base: Rounded to acute. Margin: Serrulate. Texture: Upper surface, smooth; lower surface, slightly pubescent. Color: Young foliage, upper surface: Between grayed purple, 187A to and black, 202A. Young foliage, lower surface: Between grayed purple, 187A, and black, 202A. Mature foliage, upper surface: Between grayed purple, 187A and black, 202A. Leaf color does not fade during the summer and takes on a metallic sheen towards the end of the summer. Mature foliage, lower surface: Dark brown, 200B. Venation, upper surface: 177A. Venation, lower surface: 200B. Petiole: Length: About 4 mm. Diameter: About 3 mm. Color: 177A.

Flower description:

*Flower type and habit.*—Terminal or axillary; funnel-shaped to campanulate in shape; flowers arranged singly or in small cymes. Typically about 2 to 8 flowers per node with hundreds of flowers per plant. Flowers persistent.

*Flower lastingness.*—Very long-lived; flowers last about four to eight weeks depending on temperature.

*Natural flowering season.*—Continuously flowering from May to June.

*Fragrance.*—None detected.

*Flower buds.*—Length: About 4 cm. Diameter: About 9 mm. Shape: Funnel-shaped.

*Flower size.*—Diameter: About 1.75 cm. Depth (height): About 3.5 cm.

*Petals.*—Length: About 7.5 mm. Width: About 1 cm. Quantity: Five; slightly, overlapping. Shape: Reniform; rounded. Apex: Rounded. Margin: Slightly undulate. Texture: Smooth; wavy. Color: Upper surface, when opening: 66C. Lower surface, when opening: 61A. Upper surface, opened flower: 66D to 66C, becoming 61A with subsequent development. Lower surface, opened flower: 60D.

*Sepals.*—Calyx length: About 7 mm.

*Calyx diameter: About* 1.5 mm. Quantity: Five. Shape: Linear to lanceolate. Apex: Acuminate. Margin: Entire to serrulate. Color, upper and lower surfaces: 59A.

*Peduncle.*—Length: About 1 cm. Strength: Flexible. Color: 59A.

*Reproductive organs.*—Stamens: Stamen number: Five. Anther shape: Elongated. Anther length: About 5 mm. Pollen color: 160D. Pistils: Pistil number: One. Pistil length: About 3.5 cm. Stigma shape: Two to three-parted. Stigma color: 160A. Style length: About 3.4 cm. Style color: 186C.

*Seed.*—Not observed.

Disease resistance: Under commercial conditions, plants of the new Weigela are relatively resistant to pathogens common to other cultivars of Weigela known to the Inventor.

It is claimed:

1. A new and distinct cultivar of Weigela plant named 'Elvera', as illustrated and described.

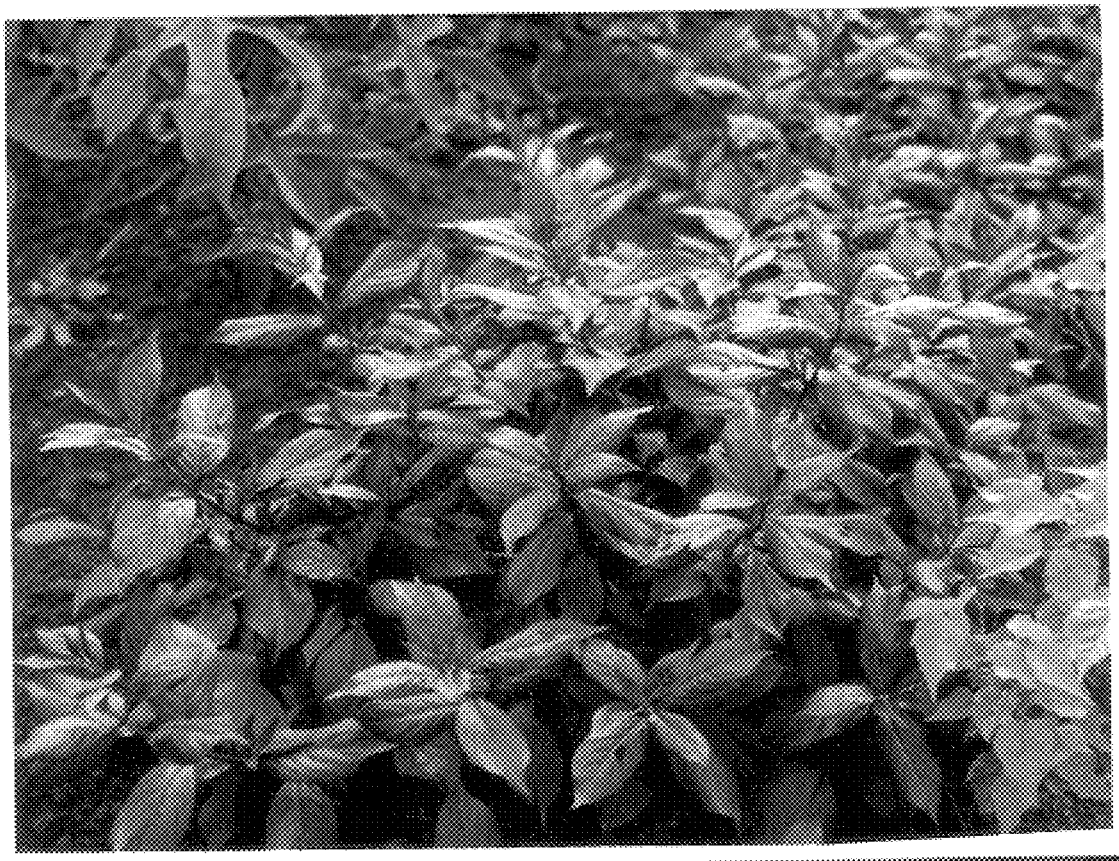
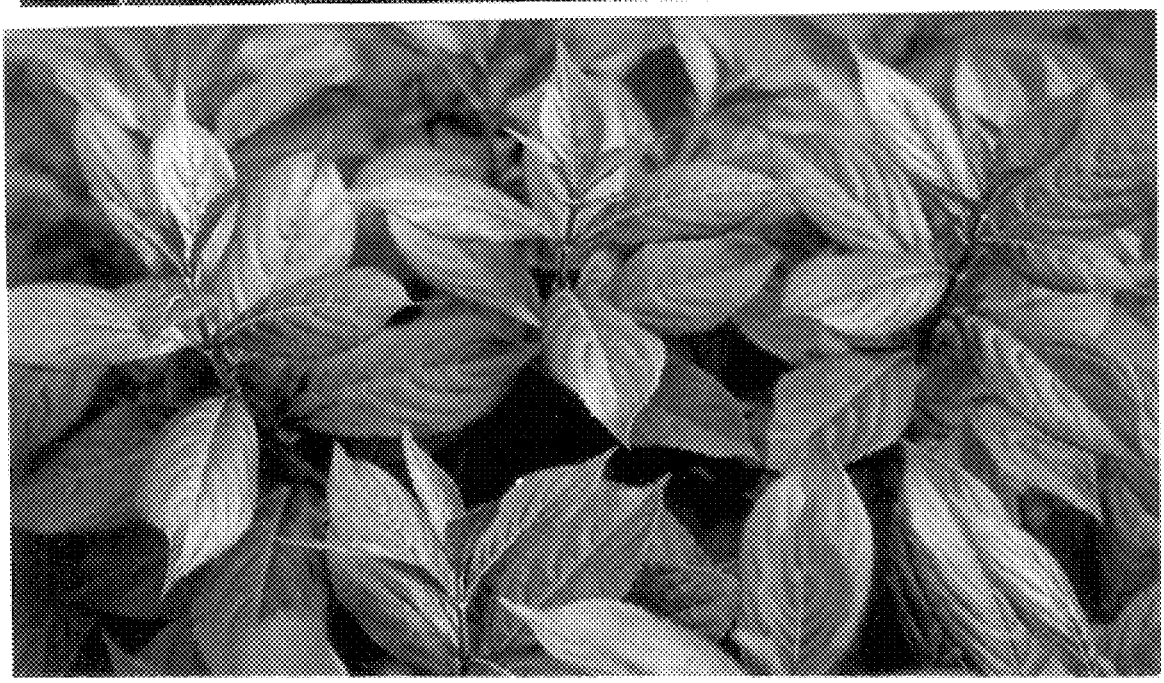

* * * * *